United States Patent
Sarfaty et al.

(10) Patent No.: US 9,554,743 B2
(45) Date of Patent: Jan. 31, 2017

(54) METHODS FOR OPTICAL IDENTIFICATION AND CHARACTERIZATION OF ABNORMAL TISSUE AND CELLS

(75) Inventors: Moshe Sarfaty, Cupertino, CA (US); Amir Lev, Cupertino, CA (US)

(73) Assignee: LS BIOPATH, INC., Saratoga, CA (US)

(*) Notice: Subject to any disclaimer, the term of this patent is extended or adjusted under 35 U.S.C. 154(b) by 500 days.

(21) Appl. No.: 12/650,437

(22) Filed: Dec. 30, 2009

(65) Prior Publication Data

US 2010/0106025 A1    Apr. 29, 2010

Related U.S. Application Data

(63) Continuation of application No. 12/525,006, filed as application No. PCT/US2008/052608 on Jan. 31, 2008.

(Continued)

(51) Int. Cl.
*A61B 6/00* (2006.01)
*A61B 5/00* (2006.01)
(Continued)

(52) U.S. Cl.
CPC ............ *A61B 5/415* (2013.01); *A61B 5/0075* (2013.01); *A61B 5/0084* (2013.01); *A61B 5/418* (2013.01); *G01J 3/0218* (2013.01); *G01J 3/0291* (2013.01); *G01J 3/44* (2013.01); *G01N 21/658* (2013.01); *A61B 5/0091* (2013.01); *A61B 2562/0233* (2013.01); *A61B 2562/16* (2013.01)

(58) Field of Classification Search
CPC ..... A61B 5/0075; A61B 5/0084; A61B 5/415; A61B 5/18; G01J 3/0218; G01J 3/44; G01J 3/0291

USPC .................................. 356/300; 600/407–480
See application file for complete search history.

(56) References Cited

U.S. PATENT DOCUMENTS 4,136,929 A * 1/1979 Suzaki ................. G02B 6/2826
                                                      359/900
5,810,742 A    9/1998 Pearlman
(Continued)

FOREIGN PATENT DOCUMENTS

JP    2001238862 A2    9/2001
WO       9215008 A1    9/1992
(Continued)

OTHER PUBLICATIONS

Guo et al., "Silver nanoparticles doped silica nanocomposites coated on an optical fiber for ammonia sensing", Sensors and Actuators B 123 (2007) 578-582; Available online Nov. 2006.*

*Primary Examiner* — Joseph M Santos Rodriguez
(74) *Attorney, Agent, or Firm* — Shartsis Friese LLP; Cecily Anne O'Regan

(57) ABSTRACT

An optical system and apparatus for the diagnosis of a biological sample is disclosed. An embodiment of the apparatus includes an optical probe, a probe head distally connectable to the optical probe, the optical probe further comprising at least one optical element for applying an electromagnetic radiation of a first wavelength to the biological sample, and one or more collection elements positioned proximate the at least one optical element; and an analyzer for analyzing a signal received from the biological sample by the one or more collection elements.

9 Claims, 8 Drawing Sheets

Related U.S. Application Data

(60) Provisional application No. 60/898,683, filed on Feb. 1, 2007.

(51) Int. Cl.
  *G01N 21/65* (2006.01)
  *G01J 3/44* (2006.01)
  *G01J 3/02* (2006.01)

(56) References Cited

U.S. PATENT DOCUMENTS

| | | | |
|---|---|---|---|
| 6,002,471 A * | 12/1999 | Quake | 356/73 |
| 6,008,889 A | 12/1999 | Zeng et al. | |
| 6,055,452 A | 4/2000 | Pearlman | |
| 6,069,689 A | 5/2000 | Zeng et al. | |
| 6,213,998 B1 * | 4/2001 | Shen et al. | 606/10 |
| 6,271,913 B1 | 8/2001 | Jung et al. | |
| 6,308,097 B1 | 10/2001 | Pearlman | |
| 6,421,559 B1 | 7/2002 | Pearlman | |
| 6,560,480 B1 | 5/2003 | Nachaliel et al. | |
| 6,678,552 B2 | 1/2004 | Pearlman | |
| 6,721,058 B2 | 4/2004 | Kim et al. | |
| 6,788,966 B2 | 9/2004 | Kenan et al. | |
| 6,845,264 B1 | 1/2005 | Skladnev et al. | |
| 6,859,282 B1 | 2/2005 | Weber et al. | |
| 6,928,315 B1 | 8/2005 | Nachaliel | |
| 6,993,383 B2 | 1/2006 | Assenheimer | |
| 7,103,401 B2 * | 9/2006 | Schomacker et al. | 600/476 |
| 7,141,019 B2 | 11/2006 | Pearlman | |
| 7,162,291 B1 | 1/2007 | Nachaliel | |
| 7,419,487 B2 | 9/2008 | Johnson et al. | |
| 8,417,328 B2 | 4/2013 | Sarfaty et al. | |
| 8,437,845 B2 | 5/2013 | Sarfaty et al. | |
| 2002/0094528 A1 | 7/2002 | Salafsky | |
| 2002/0183645 A1 | 12/2002 | Nachaliel | |
| 2003/0038951 A1 | 2/2003 | Kim et al. | |
| 2004/0015215 A1 * | 1/2004 | Fredricks et al. | 607/96 |
| 2004/0077944 A1 | 4/2004 | Steinberg et al. | |
| 2004/0143162 A1 | 7/2004 | Krattiger et al. | |
| 2004/0210158 A1 | 10/2004 | Organ et al. | |
| 2005/0065418 A1 | 3/2005 | Ginor | |
| 2005/0101876 A1 | 5/2005 | Pearlman | |
| 2007/0020144 A1 * | 1/2007 | Du et al. | 422/58 |
| 2007/0129615 A1 | 6/2007 | Backman et al. | |
| 2007/0225579 A1 * | 9/2007 | Lucassen et al. | 600/310 |
| 2008/0281314 A1 | 11/2008 | Johnson et al. | |
| 2009/0118605 A1 * | 5/2009 | Van Duyne et al. | 600/365 |
| 2013/0230883 A1 | 9/2013 | Sarfaty et al. | |

FOREIGN PATENT DOCUMENTS

| | | |
|---|---|---|
| WO | WO0152731 A1 | 7/2001 |
| WO | WO0232335 A1 | 4/2002 |
| WO | 2005032361 A2 | 4/2005 |
| WO | 2005111558 A1 | 11/2005 |
| WO | WO2005110218 A1 | 11/2005 |
| WO | 2006076810 A1 | 7/2006 |
| WO | WO2008095075 A1 | 8/2008 |
| WO | WO2008095108 A1 | 8/2008 |

* cited by examiner

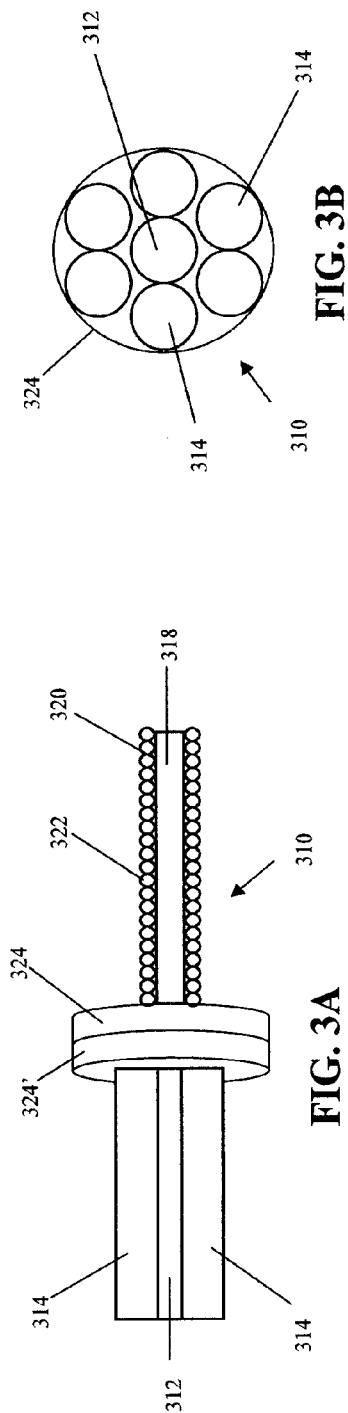
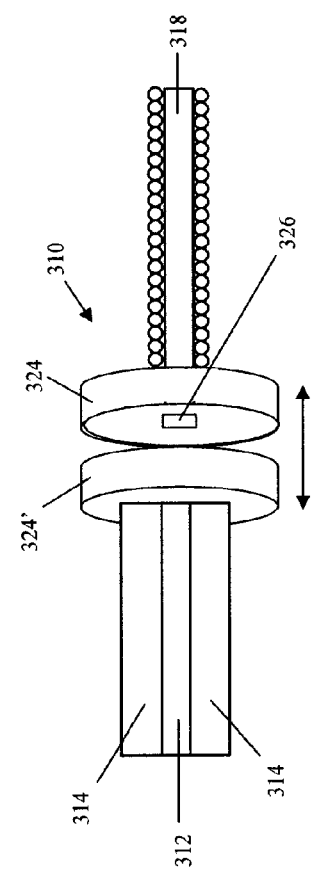
FIG. 3A
FIG. 3B
FIG. 3C
FIG. 3D

METHODS FOR OPTICAL IDENTIFICATION AND CHARACTERIZATION OF ABNORMAL TISSUE AND CELLS

CROSS-REFERENCE

This application claims is a continuation application of U.S. patent application Ser. No. 12/525,006 with an International Filing Date of Jan. 31, 2008, which claims the benefit of PCT/US2008/052608 filed on Jan. 31, 2008, under 35 USC §365, this application also claims the benefit of U.S. Provisional Application No. 60/898,683, filed Feb. 1, 2007, entitled "Optical System for Identification and Characterization of Cancer Cells" which application is incorporated herein by reference.

BACKGROUND OF THE INVENTION

The invention relates generally to diagnostic methods for real time diagnosis of biological cells and tissue. A diagnosis of abnormal tissue can be made by the detection of differences in properties of biological cells, properties such as cell density, size and composition. A diagnosis of abnormal tissue may also include a characterization of these differences in cellular properties. In addition to aiding a health care provider with making a diagnosis of abnormal tissue, an apparatus for diagnosis that provides real-time imaging ensures that the abnormal tissues is also completely removed during a surgical procedure so that the subject does not have to undergo multiple surgical procedures to remove all traces of the abnormal tissue. Typically it takes 2 to 5 days to obtain a conclusive answer on the surgical success which is determined after detailed pathology and histology analysis is performed on the sample. Real-time detection would give feedback to the surgeon during the surgery and thereby reducing the possibility that the subject will have to undergo a $2^{nd}$ surgery due to the presence of "positive margins", or not enough cancer-free margins on the excised tissue.

Current devices and methods for detecting abnormal tissue in a sample have several disadvantages. The methods currently used, include X-rays, ultrasound imaging, magnetic resonance imaging, thermal imaging, radiofrequency (RF) reflection and absorption, and electrical impedance techniques. Electrical impedance techniques has the disadvantage that the detection of abnormalities in the tissues and the cells is done by measuring the changes in electrical impedance of the tissue globally rather than measuring electrical impedance locally because the current devices and methods are positioned outside of the body when in use. Apparatuses that use global measures to detect changes in electrical impedance are less sensitive and have relatively poor spatial resolution. For example, in X-ray imaging the sensitivity of the device in imaging small-size cancer lumps such as lumps that are less than 3 mm in size is low. Additionally, in cases where there is a low relative amount of malignant cells adjacent to benign cells, the sensitivity of the X-ray is less than 30%. X-rays are also affected by any other objects that may absorb the X-rays, such as a dense tissue structures or bone located between the X-ray source and the detector. Additionally, an X-rays machine cannot be used inside the body.

Another technique for detecting the presence of abnormal tissue is the use of ultrasound waves to detect cancer cells. Ultrasound machines image tissue by looking at the reflection of the ultrasound waves of the denser cells. Also the elasticity differences between benign and malignant cells contribute to the image produced by ultrasound. The use of ultrasound is further limited in the minimum size of detectable abnormal tissue because ultrasound imaging of smaller sizes is subject to poorer signal to noise ratio. Similarly, it is also difficult to detect changes in cell density of the tissue in denser media.

Another imaging apparatus used to detect the presence of abnormal tissue is the MRI machine. Like the other imaging apparatuses previously mentioned, MRI images are also affected by cell density and composition. Further, the MRI image is strongly affected by the amount of background noise from the overall tissue scanned and is also limited by the size of abnormal tissue that is detectable. And like X-ray, MRI cannot be used inside of the body.

Other imaging methods include: thermal imaging techniques which detect changes in the temperature of tissues that have denser cell densities and which attract more blood flow to the area; RF reflection and absorption, which is also used to detect cancer cells by detecting variations in the reflection and absorption of RF in suspect tissues as compared to benign cells; electrical impedance techniques have also been developed to determine the malignancy of the cells within the organ by monitoring electrical responses from the outer surface of the tissue.

Sometimes a tissue requires further analysis. For example, it may be beneficial to know whether a sample of abnormal cells is benign or malignant. It may, therefore, be necessary to send the sample out for analysis to a pathology lab. In the pathology lab, cancerous cells are characterized using histological methods which can be time consuming and may involve complex sample preparation procedures that can last anywhere from 8-12 hours.

Because the current techniques mentioned above are typically capable only of being positioned outside of the body there may be difficulty in detecting small volumes of abnormal tissue or testing small sample areas. Also, positioning the detecting device outside of the body creates the potential for a greater amount of interference with neighboring tissue; makes it more difficult to reach the target tissue through structures in between the target tissue and the testing device; and increase the likelihood that the signal to noise ratio will be poor. In addition, the current methods for detecting abnormal tissue employ bulky machinery. Further, tissue samples are currently sent to pathology labs for testing which ultimately increases the time frame for making a diagnosis.

A method currently being used for detecting and identifying variations in samples is the optical detection of cellular variations. Optical techniques for diagnosing include the use of Surface Enhanced Raman Spectroscopy (SERS) as applied to tissues. Raman spectroscopy has been shown to have very good sensitivity down to the single cell level. In SERS electromagnetic radiation is introduced to a sample through an optical probe. Treating the surface of the structure for holding the sample with electrically conductive, metallic materials enhances the electromagnetic field experienced by the sample. The electromagnetic radiation interacts with the sample and is scattered and reflected back to a detector due to inherent properties of the sample. The scattered electromagnetic radiation can be used as an indicator of the characteristics of the tissue sample. This technique has been shown to have good sensitivity and specificity for cancer cells. However, the technique works on thin tissue sections and requires the use of a microscopy set-up.

Thus, there exists a need for optical devices and methods that detect in real-time the near-field effects of electromagnetic radiation on abnormal tissue with high sensitivity and precision and which is capable of being contained in a compact unit that is easily manipulated in reference to the sample. In addition to the advantage that the invention described herein provides real-time diagnosis of the sample being tested, an automated real-time diagnosis instrument will help to eliminate the possibility of human error or missing a critical volume of tissue.

SUMMARY OF THE INVENTION

An aspect of the invention is directed to an apparatus for the diagnosis of a biological sample. The apparatus is comprised of an optical probe; a probe head distally connectable to the optical probe, the optical probe further comprising at least one optical element for applying an electromagnetic radiation of a first wavelength to the biological sample, and one or more collection elements positioned proximate the at least one optical element; and an analyzer for analyzing a signal received from the biological sample by the one or more collection elements. The probe head can be removable from the probe, if desired. Alternatively, the probe head can be integrally formed with the probe. In some configurations, the apparatus further comprises a plurality of serially deployable probe heads, each probe head comprising one or more optical elements, the one or more collection elements positioned proximate the one or more optical elements. The collection element of the apparatus can be comprised of an optical fiber with cladding. Additionally, the collection element can further comprise a spectral filter where the spectral filter is selected from the group comprising: an interference filter, low pass filter, high-pass filter, band pass filter, and Rayleigh filter. The optical element of the apparatus can be comprised of an optical fiber with a clad segment and a bare clad-less segment. The clad-less segment of the optical element can have conductive islands of film deposited on its surface. In some cases the apparatus has an optical element with a cross-section less than 500 microns. In some cases the optical element of the apparatus is less than 5 m in length. The optical element may further be adapted to be in communication with an excitation source selected from one or more of a laser, a laser array, a light emitting diode, a diode array a broad light source, and a low pressure lamp. The apparatus can be configured to further comprise at least one of a spectrometer, an interference filter, a low-pass filter, a high-pass filter, and a band-pass filter. The analyzer of the apparatus can collect the resulting Raman scattering of the electromagnetic radiation generated by the optical element and analyze at least one signal received by the collection elements from the sample in real-time. The analyzer is further adapted and configured to identify a signature of the signal received from the biological sample. The signature of the biological sample is determined based on one or more of a density, shape, size, and chemical composition of the biological sample measured. In some configurations, the apparatus further comprises a photodetector where the photodetector collects the signal from the collection element and is at least one of a charge-coupled device camera, photodiodes, avalanche photodiodes, phototransistors, photomultipliers, charge injection device detector, and hybrid multiplier. In some configurations, the apparatus is adapted and configured to be handheld. In addition, the apparatus can be adapted and configured for use in situ. Alternatively, the apparatus can be adapted and configured for use with an endoscope. In another embodiment of the device, a metrology unit can also be provided with the device. When a metrology unit is used, the metrology unit scans an extracted biological sample in three dimensions at different locations. An apparatus with a metrology unit can further consist of a motorized stage adapted and configured to receive a mounted biological sample.

Another aspect of the invention is directed to an apparatus for in situ determination of surgical efficacy, comprising: an optical probe adapted and configured to engage a target tissue site of a mammal at a distal end, a probe head distally connectable to the optical probe, the optical probe further comprising at least one optical element for applying an electromagnetic radiation of a first wavelength to a tissue at a surgical site of a mammal, and one or more collection elements positioned proximate the at least one optical element; and an analyzer for comparing a signal received from the tissue at the tissue site by the one or more collection elements with a reference signal from a benign tissue sample. The probe head can be removable from the probe, if desired. Alternatively, the probe head can be integrally formed with the probe. In some configurations the apparatus comprises a plurality of serially deployable probe head each probe head comprising one or more optical elements, the one or more collection elements positioned proximate the one or more optical elements. The collection element of the apparatus can be comprised of an optical fiber with cladding. Additionally, the collection element can further comprise a spectral filter where the spectral filter is selected from the group comprising: an interference filter, low pass filter, high-pass filter, band pass filter, and Rayleigh filter. The optical element of the apparatus can be comprised of an optical fiber with a clad segment and a bare clad-less segment. The clad-less segment of the optical element can have conductive islands of film deposited on its surface. In some cases the apparatus has an optical element with a cross-section less than 500 microns. In some cases the optical element of the apparatus is less than 5 m in length. The optical element may further be adapted to be in communication with a an excitation source selected from one or more of a laser, a laser array a light emitting diode, a diode array a broad light source, and a low pressure lamp. The apparatus can be configured to further comprise a detector where the detector is at least one of a spectrometer, an interference filter, a low-pass filter, a high-pass filter, and a band-pass filter. The analyzer of the apparatus can collect the resulting Raman scattering of the electromagnetic radiation generated by the optical element and analyze at least one signal received by the collection elements from the tissue at a surgical site in real-time. The analyzer is further adapted and configured to identify a signature of the signal received from the biological sample. The signature of the biological sample is determined based on one or more of a density, shape, size, and chemical composition of the biological sample measured. In some cases, the apparatus can further comprise a detector where the detector is one or more of a charge-coupled device camera, photodiodes, avalanche photodiodes, phototransistors, photomultipliers, charge injection device detector, and hybrid multipliers. In some configurations, the apparatus is adapted and configured to be handheld. In addition, the apparatus can be adapted and configured for use in situ. Alternatively, the apparatus can be adapted and configured for use with an endoscope.

Also described herein is a method of diagnosing a biological sample real-time comprising: engaging the biological sample with an optical probe having a probe tip distally connectable to the optical probe, the optical probe further comprising at least one optical element adapted to apply electromagnetic radiation of a first wavelength to the biological tissue of a mammal, and one or more collection elements positioned proximate the one or more optical elements; and an analyzer for analyzing a signal received from the biological sample by the one or more collection elements; emitting electromagnetic radiation of a first wavelength; collecting a signal from the biological sample; analyzing the signal received from the biological sample to produce a result; and diagnosing the biological sample based on the result. The method may also further comprise the step of replacing the probe head with a second probe head and thereafter emitting electromagnetic radiation of a second wavelength, collecting the signal from the biological sample, analyzing the signal received from the biological sample to produce a result, and diagnosing the biological sample based on the result. The electromagnetic radiation of the first wavelength and the electromagnetic radiation of the second wavelength comprise the same wavelength. The step of engaging the biological sample can be done by applying the optical probe to a tissue site within a body of a mammal. Alternatively, the method may further comprise approaching a tissue site within a body of a mammal with the optical probe. Another alternative of the method further comprises inserting the optical probe into a body of a mammal through an endoscope. The method of diagnosing may further comprise the step of analyzing the signal in real-time. Additionally, the method of diagnosing further comprises the step of comparing the signal received from the biological sample to a signal of a reference sample. The reference sample could be a benign tissue sample and could be obtained from the same mammal.

Also contemplated is a kit for diagnosing a biological tissue comprising: an optical probe; and a probe head for use with the optical probe, the probe head comprising at least one or more optical elements adapted to apply electromagnetic radiation of a first wavelength, and one or more collection elements positioned proximate the at least one or more optical elements. The kit may further comprise a plurality of optical probe heads connectable to the optical probe.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a side view of an optical device; FIG. 3B illustrates the device of FIG. 3A as viewed from the front; FIG. 3C illustrates a side-view of a device with an interchangeable fiber tip; FIG. 3D illustrates the device being used with a sample plate.

DETAILED DESCRIPTION OF THE INVENTION

The devices, apparatuses, methods, and kits described herein are adapted and configured to rapidly determine the spatial location of abnormalities in a sample, such as a biological sample, or any soft material that can be probed. For example, the sample can come from any mammal or warm blooded animal which can serve as a sample donor. The devices, systems, methods, and kits described herein are able to discriminate between different types of cells using near-field Surface Enhanced Raman Spectroscopy (SERS) technology to identify the molecular signature of the biological cells. In Raman spectroscopy, the scattering of electromagnetic radiation by the sample is detected and the spectrum of radiation can be used to identify and characterize the sample. The optical device uses a fiber optic bundle array to guide electromagnetic radiation from an electromagnetic radiation source to the sample. The fiber optic bundle array further collects the scattered radiation from sample after being excited by the laser. The pattern of scattered radiation changes depending on the characteristics of the sample. As an example, in comparison to normal cells, cancer cells tend to be of different size and shape, their nuclei tend to be larger and more prominent, they form more dense collections of cells, they have irregular boundaries and surface topography, and they vary in chemical composition. These variations can all affect the spectral footprint of the cells being tested. The Raman spectrum from a benign reference sample of the patient's tissue can be used as a comparison for suspect samples. A comparison with a known benign sample can be used to characterize and identify abnormalities in the tissue. The statistical analysis of a collected Raman spectrum provides a unique signature of the sample based on the specific density, shape, size, and chemical composition of the measured sample.

The optical device and technique described herein can be used in the operating room during surgery to get a fast or real-time diagnosis of areas suspected of cancer or other abnormalities. In addition, the optical device and methods can be used as a time saving measure in pathology labs to characterize the sample before further histological processing.

Therefore, the present invention implements real-time diagnosis and characterization of abnormal tissues or cells in a sample where the detection and characterization of the abnormal tissues or cells can be performed either in vivo or inside the body, in vitro or outside the body, or in situ, in which the sample being tested is in an tissue extracted from a patient in which sample is located.

I. DEVICES

Figure 1:
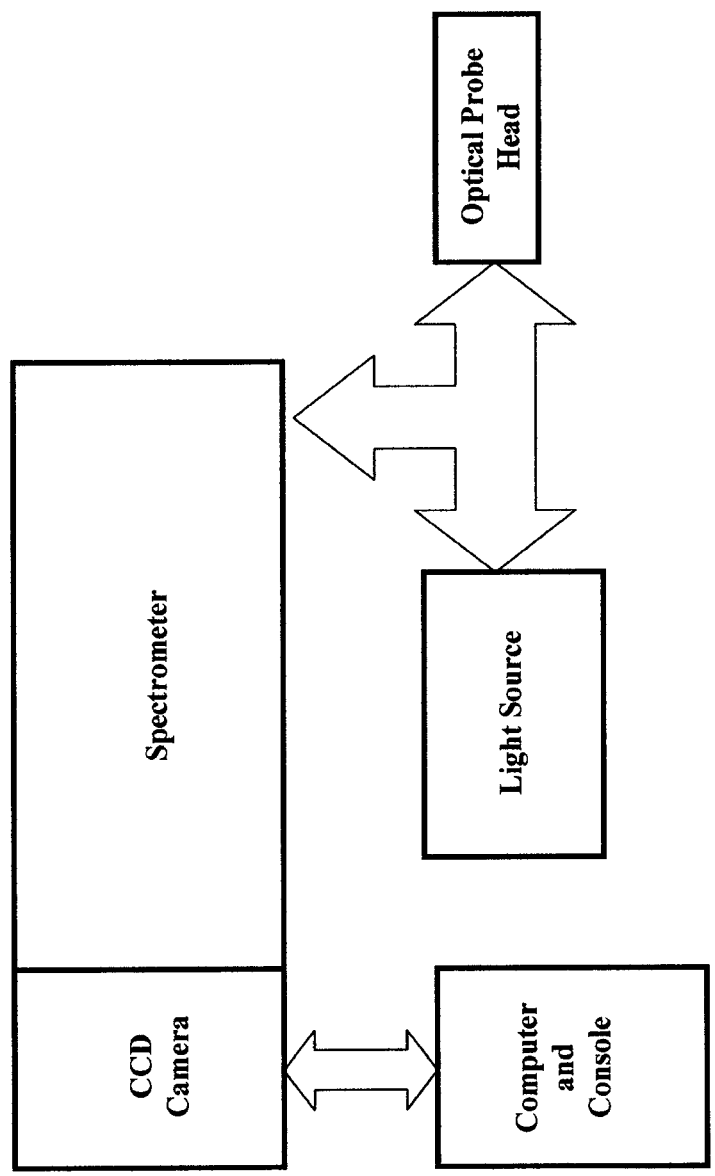
FIG. 1 is a block diagram of the components of a typical Raman spectroscopy system.

FIG. 1 is a flow diagram of the basic components of a typical Raman spectroscopy system. Typically, in such a system a light source is directed at a sample through some optical configuration. In FIG. 1 the light source is directed at the sample through the optical probe head of the optical probe. The optical probe head also serves to collect the scattered light from the sample and transmits the collected signal to an attached spectrometer. A filter, such as a Rayleigh filter, can be used to segregate the excitation source from the signal emitted from the sample. As shown in FIG. 1, the spectrometer is typically equipped with a charge-coupled device (CCD) camera, which will be used to capture the Raman spectra emitted from the tissue. The CCD at the spectrometer output which then transmits the spectral information to a console typically consisting of a computer and some kind of display unit, such as a monitor. The measured Raman spectrum is analyzed by the computer.

Figure 2:
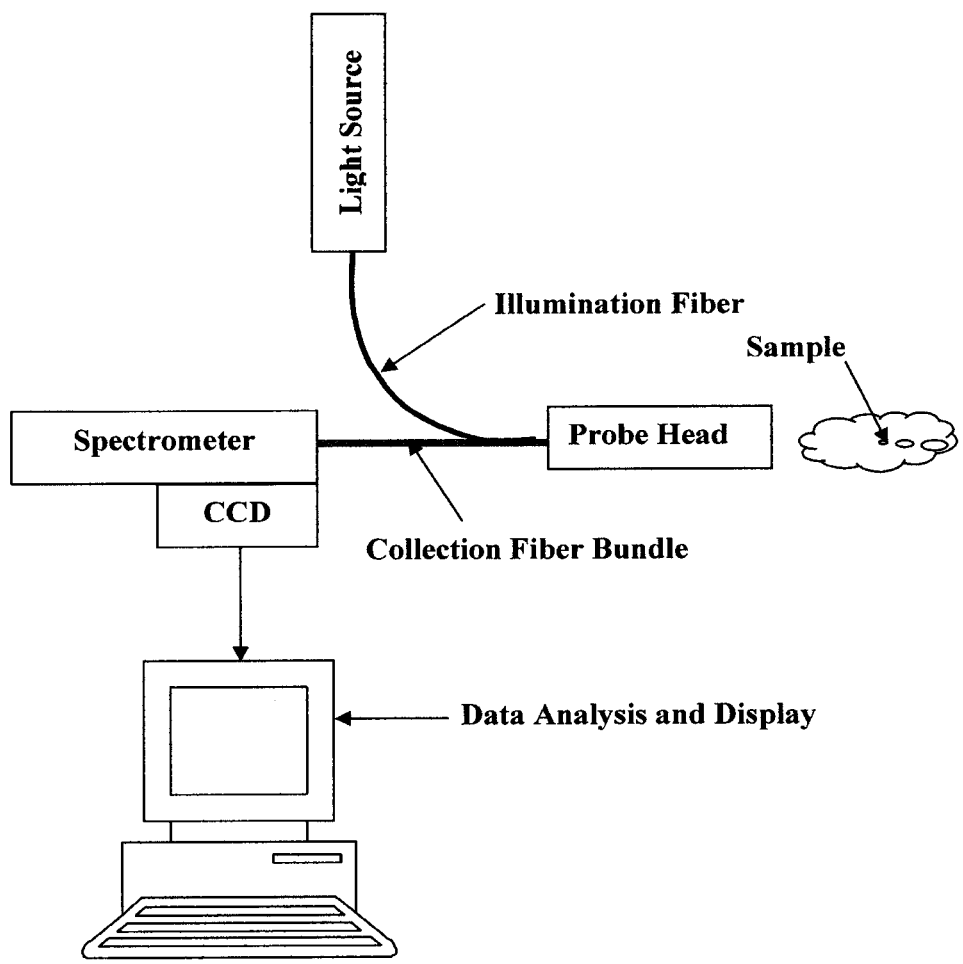
FIG. 2 illustrates a block diagram of the electrical components of the optical system.

A diagram of the typical components of a Raman spectroscopy system used with the optical device described herein is shown in FIG. 2. FIG. 2 illustrates how the illumination fiber from the light source combines with the collection fiber bundle to form the optical probe that interacts with the sample. The optical probe delivers the excitation energy to the sample by the illumination fiber. The optical Raman system typically uses a laser to excite the tissue. The laser can have wavelengths of 1024 nm 785 nm, 675 nm, 635 nm, 532 nm, or any suitable wavelength required. The wavelength will be optimized per application use case and can be interchanged when required. The spectral response of the system will have high spectral resolution of 5 $cm^{-1}$ in a spectral range of 175-3100 $cm^{-1}$. When the energy or radiation from the excitation source, such as a light source, comes in contact with the sample, the radiation is scattered by the sample in all directions. The scattered light is collected by the collection fiber bundle of the optical probe. As in FIG. 1, the signal is then typically transmitted to a spectrometer coupled to a CCD camera and ultimately to a console where the Raman spectrum is analyzed by the computer and displayed on a monitor. The spectra of the scanned tissue will be compared with the reference spectrum and deviations due to malignancy or abnormality will be picked up and presented to the user.

A side view of an optical probe 310 is shown in FIG. 3A. The optical probe consists of an optical probe head 318 and a fiber bundle array 316. The probe head 318 is coupled to the fiber bundle array 316 through a connector 324, 324'. The connector 324, 324' is in a plane perpendicular to a longitudinal axis of the short decladded optical fiber. Additionally, the at least one collection element 314 is positioned proximal to the probe head 318 such that the collection element 314 is radially positioned exterior to an outer edge of the coated optical probe head 318. The probe head 318 consists of a short optical fiber decladded from its cladding and partially coated with thin metallic conductive film, which is typically gold or silver, so that the film forms conductive islands of film. The thin film islands are partially covering the tip to enable light propagation outside of the optical probe head tip 318 perpendicular to the longitudinal axis of the optical probe head 318. The island film is micro shaped to provide a larger conducting surface area to enhance the molecular Raman spectra generated by the excitation energy introduced by the optical probe head 318. In some cases the island film is shaped to form metallic nanosized beads 322 at the surface 320 of the probe head 318, as shown in FIG. 3A. The optical probe head in some cases may also be covered at the tip of the optical probe along the axial direction with a reflecting metal layer. Covering the tip of the fiber optic prevents electromagnetic radiation from being lost in the forward direction. The coated optical probe head 318 is operably connected to the light source through the illumination fiber 312 of the fiber bundle array 316 to provide local near-field amplification of the electromagnetic field used to stimulate sample. In some cases, it may be desirable to have more than illumination fiber and more than one probe head on the same optical device.

The fiber bundle array 316 consists of an illumination fiber 312, and at least one collection element 314. The illumination fiber 312 introduces excitation energy from the excitation energy source, such as a light source, to the sample. The illumination fiber is typically located at the center of the fiber bundle array 316 when more than one collection element 314 is present. FIG. 3B is a front view of the optical probe 310. As seen in FIG. 3B, when multiple collection elements are present 314, the probe head 318, and hence the illumination fiber couple to the probe head, is located in the center of the device and is surrounded by the multiple collection elements 314. In the fiber bundle, the illumination fiber is cladded to ensure that the optical signals remain internalized inside of the illumination fiber.

Once the sample is excited by the electromagnetic radiation, the radiation is scattered by the sample thereby generating a Raman spectrum for the sample. The resulting Raman spectrum is collected by at least one collection element 314. Typically the collection elements are fiber optic cables and multiple collection elements are embodied in the invention. When multiple collection elements are used, the collection elements comprise the remainder of the fiber bundle array. Similar to the illumination fiber, the collection elements 314 are cladded, to ensure that the optical signals remain internalized inside of their respective fibers.

The optical device described herein may consist of an optical probe head integrated with the fiber bundle array. The optical probe head may either combined with the fiber bundle cable to form a probe, where the probe head is permanently coupled to the fiber bundle array; the probe head alternatively may be fabricated from the illumination fiber by stripping the cladding from the illumination fiber. Alternatively, the probe head 318 can be interchangeable with other probe heads by detaching and reattaching different probe heads with the same fiber bundle array as shown in FIG. 3C. Replacing the probe head between different samples avoids cross-contamination between samples by eliminating the potential for residues that stick to the probe head surface from one sample to be passed on to subsequent samples. The connectors 324, 324' in FIG. 3C connect the probe head 318 with the fiber bundle array 316. The probe head 318 can be interchanged by detaching the probe head coupling 324 from the fiber bundler array coupling 324' as designated by the double-sided arrows. FIG. 3C also illustrates how the end 326 of the probe head 318 is centered thereby corresponding to the illumination fiber 312 when the connectors 324, 324' are coupled together. The connectors can be coupled together by any suitable means for coupling the connectors together. Examples of ways the connectors can be coupled together include, but are not limited to, adhesives, hook and loop fasteners, magnetic forces, tape, elastics, or any other suitable material for coupling the connectors together. Alternatively, the probe head can be coupled to the fiber bundle array through a screw type connector. FIG. 3D is an illustration of the optical probe head 310 used with a carrying substrate 331 for the sample. The carrying substrate 331 enhances the electromagnetic field.

Figure 4:
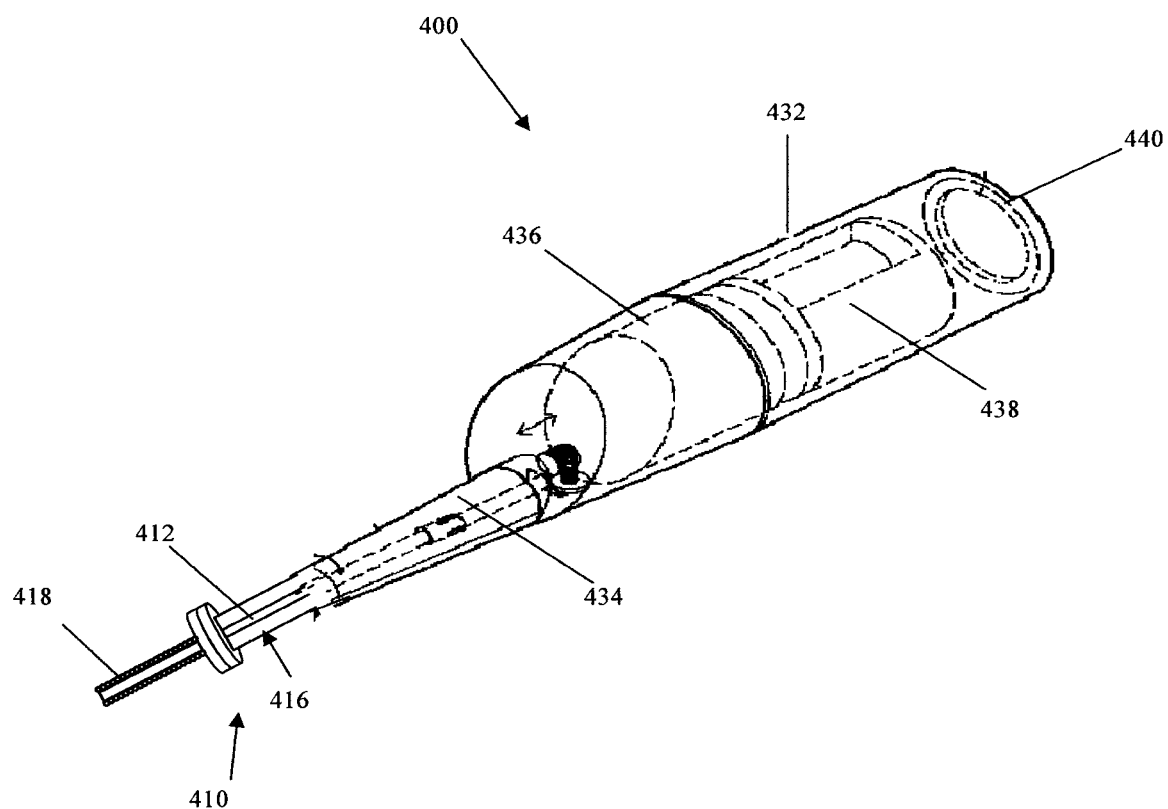
FIG. 4 illustrates a perspective view of a handheld optical device.

Although the optical probe 410 can be used by manually holding the optical probe head, it may be beneficial to introduce the optical probe 410 to the sample through the use of a handheld device 400 as shown in FIG. 4. The optical probe 410 can be directly attached to the handheld device 400. The optical probe head 418 of the optical probe 410 can be configured to the optimal size for the sample or for the abnormal tissue or cells being measured. In FIG. 4 the optical probe 410 is attached to the handle 432 of the device 400 by the neck 434. The optical probe 410 can be permanently attached to the handheld device 400. In such a configuration, the entire handheld device 400 can be disposed of in its entirety. Alternatively, the optical probe head 418 can be cleaned and sterilized and the whole device reused. In some cases, the handle 432 and the neck 434 of the device 400, and the fiber bundle array 416 are reusable while the optical probe 418 is disposable. In some cases, the optical probe head 418 and fiber bundle array 416 are disposable. In some cases, the optical probe 410 is permanently attached to the neck 434 of the device 400 and the optical probe 410 and neck 434 of the device 400 together are disposable whereas the handle 432 of the device is reusable.

To use the device 400, the user grips the handle 432 of the device 400 and approaches the sample with the optical probe 410, so that the optical probe head 418 is sufficiently proximal to the sample. Typically the handheld device 400 is configured so that the optical probe 410 is rotatable with respect to the handle 432 to ensure that the proper areas of sample are stimulated and an adequate amount of Raman scattering is detected. Further, the neck of the 434 of the device 400 is typically translatable with respect to the handle 432. The optical probe 410 can then be translated either close to or further from the handle 432 of the device 400, in other words distal to or proximal to the sample, while the handle 432 of the device 400 remains stationary.

In order to fully connect the optical probe 410 to the handle 432 of the device 400, the bundle fiber array 416 is typically fed through the neck 434 of the device 400. The illumination fiber 412 of the bundle fiber array 416 is in communication with a light source. The light source can either be external to the handheld device or the light source can be an internal light source housed within the handle 432 of the device 400 as is shown in FIG. 4. The light source 436 is further powered by a power source 438 which can also be housed within the handle 432 of the device 400.

The handheld device stimulates the sample with electromagnetic radiation or other excitation source and records the signals generated by the cells of the sample excited by the electromagnetic radiation. The signals generated by the sample when detected and recorded by the collection elements of the device can then be sent to the spectrometer which it typically located external to the handheld device. In this case, the collection fiber bundle would exit the device through the base 440 of the device 400. Alternatively, a small processor or data storage component could be housed in the handle of the device for storage of the signals detected until the data can be transferred to the spectrometer.

Figure 5A:
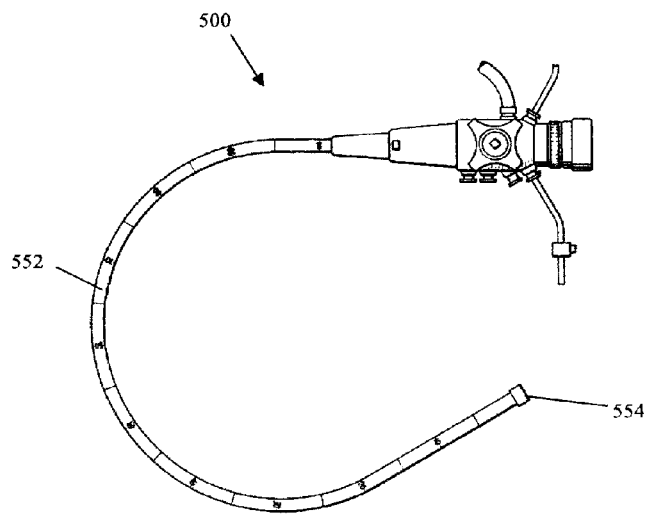
FIG. 5A is an exemplary embodiment of an endoscope.
Figure 5B:
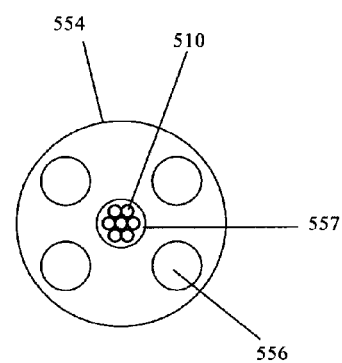
FIG. 5B illustrates a front view of the end of an endoscope.

The optical probe head can be used in a handheld unit as previously described. Alternatively, a modified version of the optical probe head can be incorporated into other medical devices. For example, the optical probe head can be incorporated into an endoscope. An exemplary illustration of an endoscope 550 is shown in FIG. 5A. Before the tube 552 is introduced into the patient, the end 554 of the endoscope 550 is outfitted with an optical device. FIG. 5B illustrates the end 554 of the tube of a 5-bore endoscope as viewed from the front and an optical device located within the center bore 557. When used together with an endoscope 550, the optical probe 510 can be inserted into one of the bores 556 of the endoscope 550. In FIG. 5B, the optical probe 510 has been inserted into the center bore 557. The remaining bores 556 remain available for the introduction of other implements. It can be appreciated that the optical probe 510 does not have to be inserted into the center bore 557 but can be inserted into any of the remaining bores 556. Additionally, although only one optical probe 510 has been inserted into the center bore 557, as in FIG. 5B, more than one optical probe 510 can be inserted into multiple bores 556 and used together simultaneously.

Figure 5C:
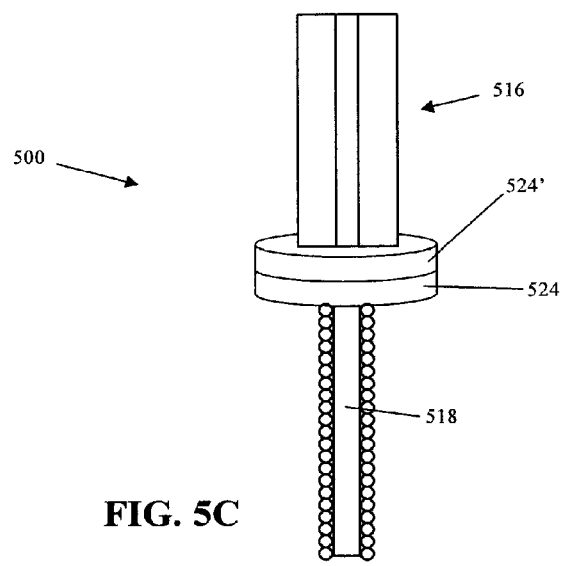
FIG. 5C illustrates a device for inserting into the endoscope.

In some cases when an optical probe head is used together with an instrument such as an endoscope, the bundle fiber array with a connector is introduced into the bore. The optical probe head 518 is then coupled to the bundle fiber array 516 through the connectors 524, 524' as shown in FIG. 5C and is then seated within the center bore 557 as shown in FIG. 5B. Alternatively the bundle fiber array may already be coupled to a probe head and the bundle fiber array together with attached probe head can be fed through the bore of the endoscope by inserting the device into the end of the endoscope proximal to the inside of the patient. Once fed through the endoscope tube, the bundle fiber array is then connected to a spectrometer located at the distal end of the endoscope.

Figure 6:
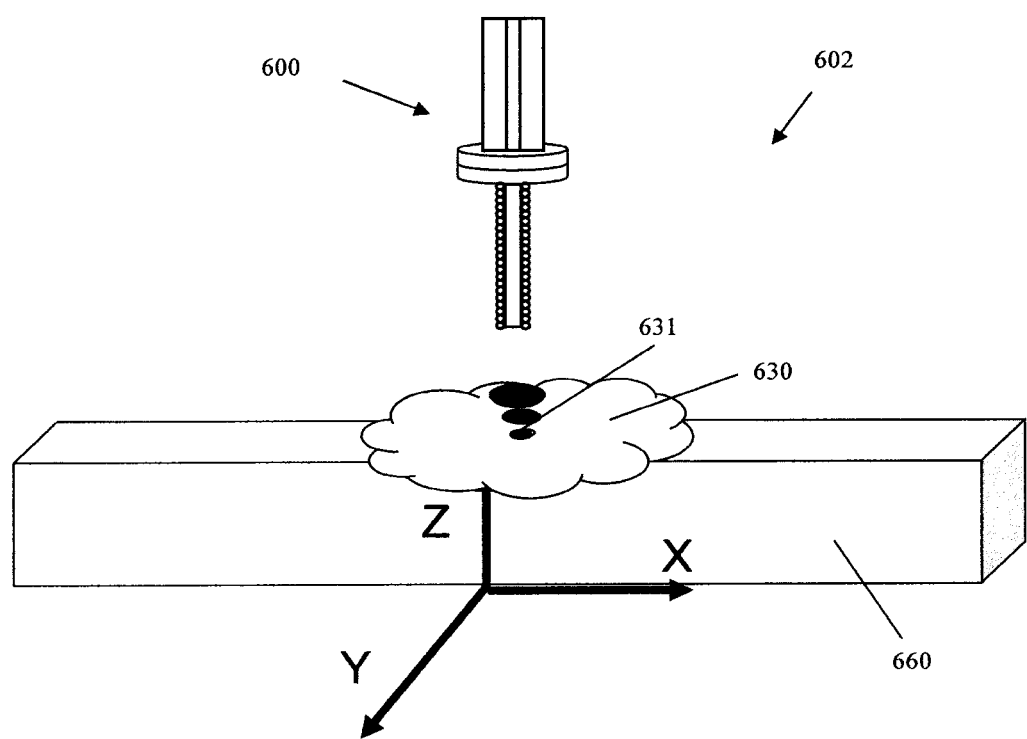
FIG. 6 illustrates an optical device in use with a metrology apparatus.

The optical device 600 described herein in some cases is used as part of a metrology apparatus 602 as shown in FIG. 6. The metrology apparatus 602 consists of a motorized stage 660 which can be used to translate the sample in three dimensions designated by the X-, Y-, and Z-axes. A sample is placed on the motorized stage 660 either directly or as a slide preparation and measurements can be made to the sample 630 through an automated system. The whole sample 630 can be scanned or the user can define the regions of the sample to be scanned. Where the user identifies or define the regions of the sample 630 to be scanned, the corresponding coordinates can be inputted into the automated system using a user interface software program. The boundaries of the sample are typically determined optically or by a specific hardware limiter that the operator will input to the automated system. The system then registers the exact coordinates to be measured and will associate the measurements with the 3D coordinates of the sample. Once the coordinates have been inputted, the device 600 is typically fixed to the metrology apparatus 602. The sample 630 is translated in XYZ directions using the motorized stage 660 through the software control. The spatially resolved results are then mapped into sample coordinates using a stage control location encoder. The 3D results are then displayed on the system monitor and "care areas" corresponding to responses of potentially malignant cells, or areas of interest 631, and their margins 629 will be highlighted compared to benign regions. The data gathered in then statistically tested and compared with a benign reference response for the specific sample. Deviations outside the normal distribution band will be highlighted. Based on the 3D image and the observed margins the surgeon will decide if the excised sample was adequate or if more tissue needs to be excised and from which location. Repeat measurements on the second sample excised will be carried out in a similar manner to assure clean margins.

Figure 7:
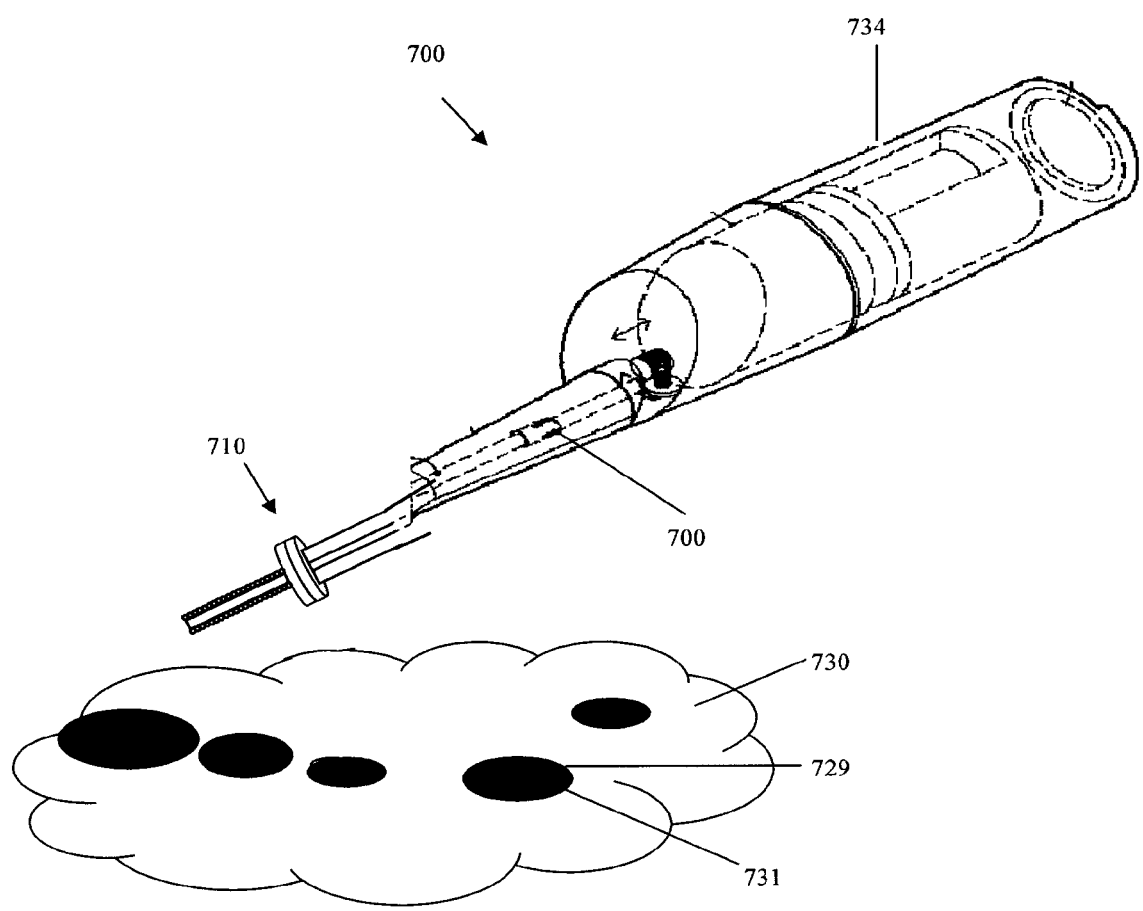
FIG. 7 illustrates a probe being used in situ.

The device can be used in vivo or in the body, in vitro or in isolated cells, or in situ, testing cells in removed intact tissue. FIG. 7 illustrates the device 700 as used in situ. As in other methods of use, a suitable optical probe 710 is attached to the handle 734 of the device 700 by the neck 732. A sample 730 with areas of interest 731 is removed from the subject. The user then uses the handle 732 to direct the optical probe head 710 to the areas of the sample 730 to be tested. The device 700 emits radiation and detects scattered radiation from the sample that designates the locations of the areas of interest 731 as the sample 730 is probed and establishes the margins 729 of the areas of interest 731. These areas of interest 731 can then be mapped in relation to the remainder of the sample 730.

Figure 8:
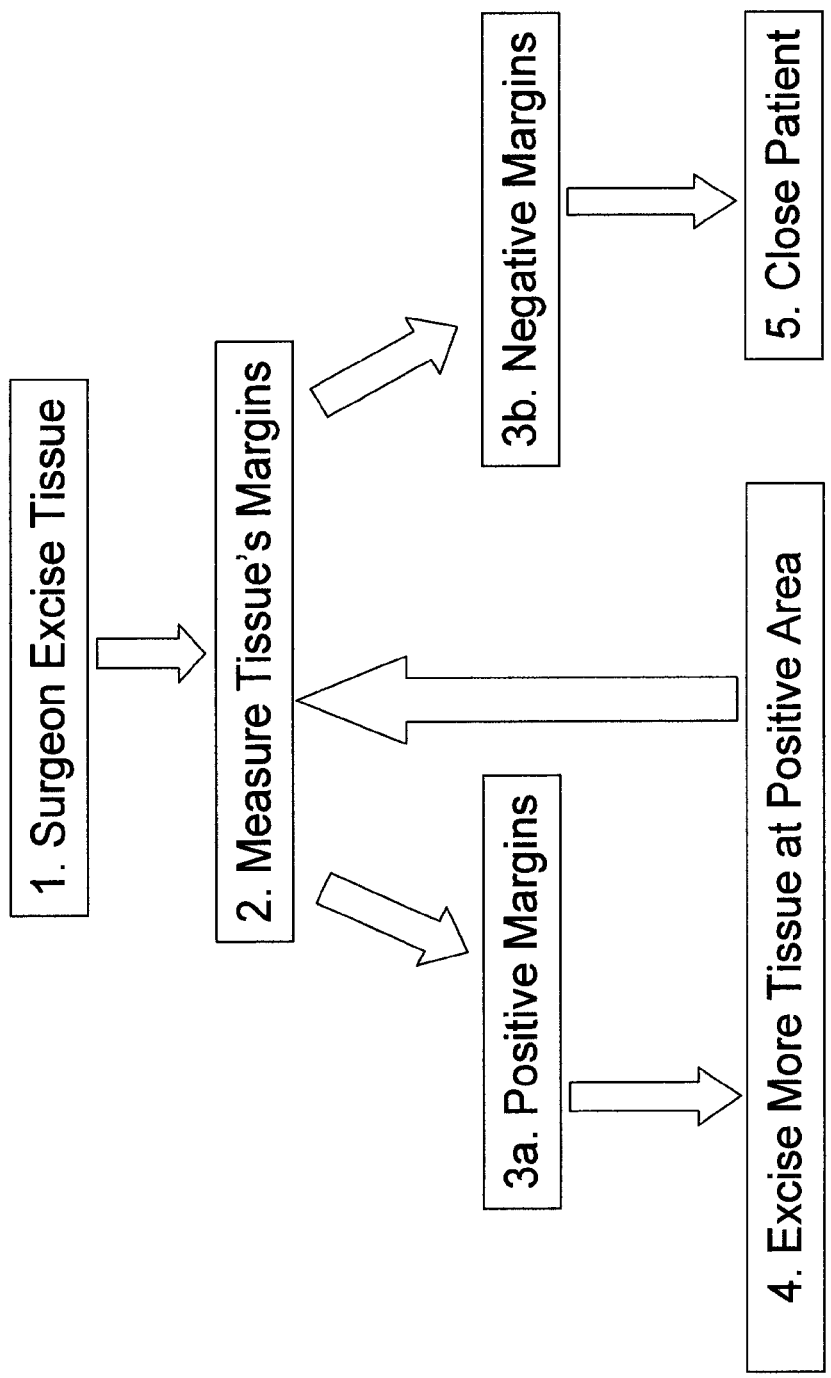
FIG. 8 is a block diagram of a method of use of the optical device.

In addition to being used to diagnose a cancerous condition by detecting abnormalities in cells, the optical device measured herein can be used in the operating room by a surgeon in real-time to ensure complete removal of problematic tissue, such as cancer cells, during a surgical procedure. FIG. 8 illustrates a flow diagram of how the device may be used to ensure removal of problematic tissue. When a patient has been diagnosed with cancer, the patient undergoes surgery to remove the tissue. Once the surgeon has gained access to the cancerous tissue, the surgeon excises the tissue from the patient. The tissue margins are then measured to detect whether the entire cancerous area has been excised. If the device indicates that the entire cancerous region has not been excised, more tissue is excised and the margins of the tissue measured again. This is repeated until the margins of the tissue excised indicate that the cancerous tissue has been excised in its entirety. Once it has been determined that the entire cancerous region has been excised, the surgeon can then close the site of the surgical incision knowing that the cancerous tissue has been completely removed.

II. KITS

Kits employing the devices, components, and materials of the invention can also be employed. A variety of kits are also contemplated. For example, a kit for diagnosing a biological tissue can comprise, for example, an optical probe and an optical probe head for use with the optical probe, the optical probe head comprising at least one or more optical elements adapted to apply electromagnetic radiation of a first wavelength, and one or more collection elements positioned proximate the at least one or more optical elements. Furthermore, the kit could include a plurality of optical probe heads connected to the probe. A kit including an embodiment of the invention previously described in some instances further includes a console component. The console component typically consists of a processor and some kind of display unit, such as a computer and a monitor. The optical characteristics detected by the device are typically displayed on the monitor.

III Methods

A variety of methods are also contemplated. One method includes a method of diagnosing a biological sample in real-time. The method comprises: engaging the biological sample with an optical probe having an optical probe head distally connectable to the optical probe, the optical probe further comprising at least one optical element adapted to apply electromagnetic radiation of a first wavelength to the biological tissue of a mammal, and one or more collection elements positioned proximate the one or more optical elements; and an analyzer for analyzing a signal received from the biological sample by the one or more collection elements; emitting electromagnetic radiation of a first wavelength; collecting a signal from the biological sample; analyzing the signal received from the biological sample to produce a result; and diagnosing the biological sample based on the result. The method can further comprise engaging the biological sample by applying the optical probe to a tissue site within the body of the mammal. Alternatively, the method can further comprise engaging the biological sample by approaching the tissue site within the body of the mammal with the optical probe. Additionally, the optical probe can be inserted into the body of the mammal through an endoscope. The optical probe head can be replaced, if desired, with a second optical probe head. The second probe head can then emit electromagnetic radiation of a second wavelength and the signal from the biological sample in response to the electromagnetic wavelength of the second wavelength can be collected and analyzed to produce a result, and thereby the biological sample is able to be diagnosed. Furthermore, the electromagnetic radiation of the first wavelength and the electromagnetic radiation of the second wavelength are the same. Alternatively, the method can further comprise the step of analyzing the signal in real-time. Further, the signal received from the biological sample can be compared to a signal received from a reference sample. For example, the reference sample can be a benign tissue sample, the benign tissue sample having been obtained from the same mammal.

III EXAMPLES

Example 1

Detection of Breast Cancer In Vitro

The optical device can be used to detect suspect areas of tissue during a lumpectomy. Once the surgeon excises the suspect breast tissue, either the surgeon, a pathologist, or lab technician in the operating room can use the handheld device as shown in FIG. 3 to investigate if the margins of the tissue are free of malignant tissue, the steps of which are shown in the FIG. 8. The user approaches the tissue with the handheld device and delivers electromagnetic radiation to the tissue at the desired location. The user than uses the device to detect and measure the electromagnetic radiation scattered by the suspected areas of tissue. A reference signal specific to the patient is collected from a clear benign portion of the tissue and the results of the benign tissue response are compared to the measurements obtained from the suspect portions of the sample. If it is determined that the suspect tissue is malignant tissue, the surgeon can follow up with excision of more tissue in the suspected area in the body. The newly excised tissue is then measured again in vitro to assure the margins are clear before closing the patient. If the margins are clear, the surgeon can then close the patient.

Example 3

Detection of Breast Cancer In Vivo

The optical device can also be used to detect cancerous tissue in vivo during a lumpectomy. During the lumpectomy, the surgeon will use the probe in the body cavity of the patient to assess if, once the suspect tissue has been excised, the remaining tissue in the breast is free of malignancy. Once the excision procedure is complete, the surgeon will use the device inside the body to scan the surface of the cavity. The results obtained from a benign tissue sample will be registered to form a baseline for the patient tissue response and the results from the suspect areas will be compared with the benign values. The console will display the variations in the tissue response. If the spectrum of scattered radiation from the sample varies from the spectrum from a benign sample, the surgeon will then note the area and will excise more tissue at the margins to ensure complete excision of the cancerous tissue before closing the patient.

Example 4

Sentinel and Lymph Node Detection and Excision

As part of a typical cancer excision surgery the surgeons sometime excise sentinel lymph nodes and additional nodal areas to determine whether the cancer has metastasized. The optical probe can be used in vivo, to make sure that the node is cancer free before excising it. Additionally the device can be used in-vitro to find out if more lymph nodes need to be excised before the patient is closed.

Example 5

In Situ Prostate Cancer Biopsy

Current methods for conducting a prostate cancer biopsy include taking tissue from 12 random sites in the prostate gland. The tissue taken during the biopsy is then sent to a lab and the results are obtained a few days later. If the areas of cancer are not within one of the 12 random sites, the procedure needs to be repeated again. Using the optical device described herein, in conducting a prostate cancer biopsy, the optical probe of the invention can be mounted in an endoscope and the organ suspected of cancer can be optically tested using the probe. The response can then be compared to the response from a benign area of the organ. If a noticeable deviation from the benign tissue response is detected, the surgeon will excise the tissue from this area to perform a permanent pathology.

Example 6

Optical Core Biopsy

The invention also can be used in a biopsy to determine whether a suspected area of tissue is malignant or not. Because the device operates in real time, the invention can help reduce the amount of benign biopsy procedures done today as well as reduce the cost of these procedures. It is found that more than 80% of biopsies result in the sample being benign tissue, therefore the device will be able to reduce the cost of these procedures to those tissue portions that are more likely to show malignancy.

Example 7

Combined Electrical and Optical Detection and Characterization of Abnormal Tissue The optical device can also be used with other devices for locating abnormal tissue. During a lumpectomy, the surgeon can probe the body cavity of a patient to localize the areas of abnormal tissue. The surgeon can use an electrical characterization device to narrow the surgical area. Once the area has been narrowed using the electrical device, the optical device can then be used to identify the locations of cancerous tissue without having to penetrate the tissue with a foreign object. The area can then be rescanned with the optical probe to determine if any abnormal tissue remains. If abnormal tissue is detected, the tissue can be excised. If no abnormal tissue is detected, the patient can then be closed by the surgeon.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of diagnosing cancer in a biological tissue of a patient in real-time comprising:
    contacting the biological tissue with an optical probe having a probe tip distally connectable to the optical probe, the probe tip further comprising:
    at least one application element comprising a decladded optical fiber element partially coated with metallic nanosized conductive beads on an outer surface of the decladded optical fiber element, for applying electromagnetic radiation of a first optical wavelength directly to the biological tissue, one or more separate collection elements each of the one or more separate collection elements comprising a plurality of cladded optical fibers positioned around the decladded optical fiber covered with metallic nanosized beads and having an end terminating proximate the distal end of the decladded optical fiber element, a fiber bundle array connector connected to the decladded optical fiber element at a proximal end and the one or more separate collection elements at a distal end, and further wherein the collection elements collect a near-field Surface Enhanced Raman Spectroscopy (SERS) response signal from the biological tissue in response to the applied electromagnetic radiation, reflected from the biological tissue, and a computer configured to analyze a spectrum of the response signal received from the biological tissue by the one or more separate collection elements;
    emitting electromagnetic radiation of a first wavelength along a length of the decladded optical fiber element in a direction perpendicular to the longitudinal axis of the decladded optical fiber;
    collecting the near-field Surface Enhanced Raman Spectroscopy response signal from the biological tissue through the collection elements;
    analyzing, with the computer, the collected near-field Surface Enhanced Raman Spectroscopy response signal received from the biological tissue to produce a real-time result to identify one or more molecular signatures of the biological tissue;
    calculate, with the computer, the normal distribution of the molecular signatures of the biological tissue; and
    determine, with the computer, a diagnosis of cancer of the biological tissue by comparing the normal distribution of the biological tissue with a benign reference tissue normal distribution.

2. The method of claim 1, wherein the step of contacting the biological tissue further comprises applying the optical probe to a tissue site within a body of a mammal.

3. The method of claim 1, wherein the step of contacting the biological tissue further comprises inserting the optical probe into a body of a mammal through an endoscope.

4. The method of claim 1 further comprising the step of identifying suspect areas of tissue with the computer for identifying and characterizing abnormal tissue and cells prior to contacting the biological tissue with the optical probe.

5. The method of claim 1, further comprising the step of replacing the probe head with a second probe tip and thereafter emitting electromagnetic radiation of a second wavelength, collecting the response signal from the biological tissue, analyzing the signal received from the biological tissue to produce a result, and diagnosing the biological tissue based on the result.

6. The method of claim 5, the electromagnetic radiation of the first wavelength and the electromagnetic radiation of the second wavelength comprise the same wavelength.

7. The method of claim 1, wherein the benign reference tissue is obtained from the same patient.

8. The method of claim 1, wherein the collection elements comprise a second set of electrodes different from the application element and the step of applying electromagnetic radiation of the first wavelength to the biological tissue of the patient, further comprises the step of sending a signal to the application element.

9. The method of claim 8, wherein the step of collecting the response signal from the biological tissue further comprises the step of collecting the signal utilizing the second set of electrodes.

* * * * *